United States Patent
Crocker et al.

(10) Patent No.: US 6,538,134 B2
(45) Date of Patent: Mar. 25, 2003

(54) 4-BENZYL-2-HYDROXY-1,4-OXAZINE-3-ONE AND POLYMORPHIC FORMS THEREOF

(75) Inventors: Louis S. Crocker, Belle Mead, NJ (US); Karel M. Jos Brands, Jersey City, NJ (US); Todd D. Nelson, East Windsor, NJ (US); Philip J. Pye, Guttenberg, NJ (US); Jonathan D. Rosen, Brooklyn, NY (US); Kai Rossen, Degussa Huls (DE)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/877,839

(22) Filed: Jun. 8, 2001

(65) Prior Publication Data

US 2002/0042510 A1 Apr. 11, 2002

Related U.S. Application Data

(60) Provisional application No. 60/210,254, filed on Jun. 8, 2000, and provisional application No. 60/210,204, filed on Jun. 8, 2000.

(51) Int. Cl.$^7$ .................. C07D 265/32; C07D 263/106
(52) U.S. Cl. ................ 544/173; 544/170; 548/215
(58) Field of Search ................ 544/170, 173; 548/215

(56) References Cited

PUBLICATIONS

Perrone et al. Synthesis 598–600, 1976.*
Le Rouzic–Bellevre, C. R. Hebd. Seances Acad. Sci., Ser. C, 282(6), 307–310, 1976.*

* cited by examiner

Primary Examiner—Venkataraman Balasubramanian
(74) Attorney, Agent, or Firm—J. Eric Thies; Melvin Winokur

(57) ABSTRACT

The present invention is concerned with 4-benzyl-2-hydroxy-1,4-oxazin-3-one, and novel processes for the preparation therof. This compound is useful as an intermediate in the synthesis of compounds which possess pharmacological activity.

14 Claims, 2 Drawing Sheets

4-BENZYL-2-HYDROXY-1,4-OXAZINE-3-ONE AND POLYMORPHIC FORMS THEREOF

This application claims benefit of U.S. Provisional application Nos. 60/200,204 and 60/210,254 both filed on Jun. 8, 2000.

BACKGROUND OF THE INVENTION

The present invention relates to 4-benzyl-2-hydroxy-1,4-oxazin-3-one which is useful as an intermediate in the preparation of certain therapeutic agents. In particular, the present invention provides 4-benzyl-2-hydroxy-1,4-oxazin-3-one which is an intermediate in the synthesis of pharmaceutical compounds which are substance P (neurokinin-1) receptor antagonists.

General processes are disclosed in the art for the preparation of compounds related to 4-benzyl-2-hydroxy-1,4-oxazin-3-one, but these result in relatively low and inconsistent yields of the desired product (A. Le Rouzic-Bleeevre, Fr. C. R. Hebd. Seances Acad. Sci., Ser. C., 282 (6) 307–310 (1976); T. Mancilla, et al., Heteroatom. Chem., 6(6) 605–609 (1995)). In contrast to the previously known processes, the present invention provides effective methodology for the preparation of 4-benzyl-2-hydroxy-1,4-oxazin-3-one in relatively high yield and purity.

It will be appreciated that 4-benzyl-2-hydroxy-1,4-oxazin-3-one is an important intermediate for a particularly useful class of therapeutic agents. As such, there is a need for the development of a process for the preparation of 4-benzyl-2-hydroxy-1,4-oxazin-3-one which is readily amenable to scale-up, uses cost-effective and readily available reagents and which is therefore capable of practical application to large scale manufacture.

Accordingly, the subject invention provides 4-benzyl-2-hydroxy-1,4-oxazin-3-one via a very simple, short, relatively inexpensive and highly efficient synthesis.

SUMMARY OF THE INVENTION

This invention is directed to the compound 4-benzyl-2-hydroxy-1,4-oxazin-3-one of the formula:

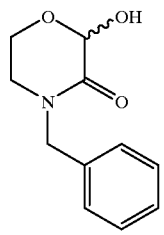

This compound is an intermediate in the synthesis of compounds which possess pharmacological activity. In particular, such compounds are substance P (neurokinin-1) receptor antagonists which are useful e.g., in the treatment of psychiatric disorders, inflammatory diseases, and emesis.

DETAILED DESCRIPTION OF THE INVENTION

Figure 1:
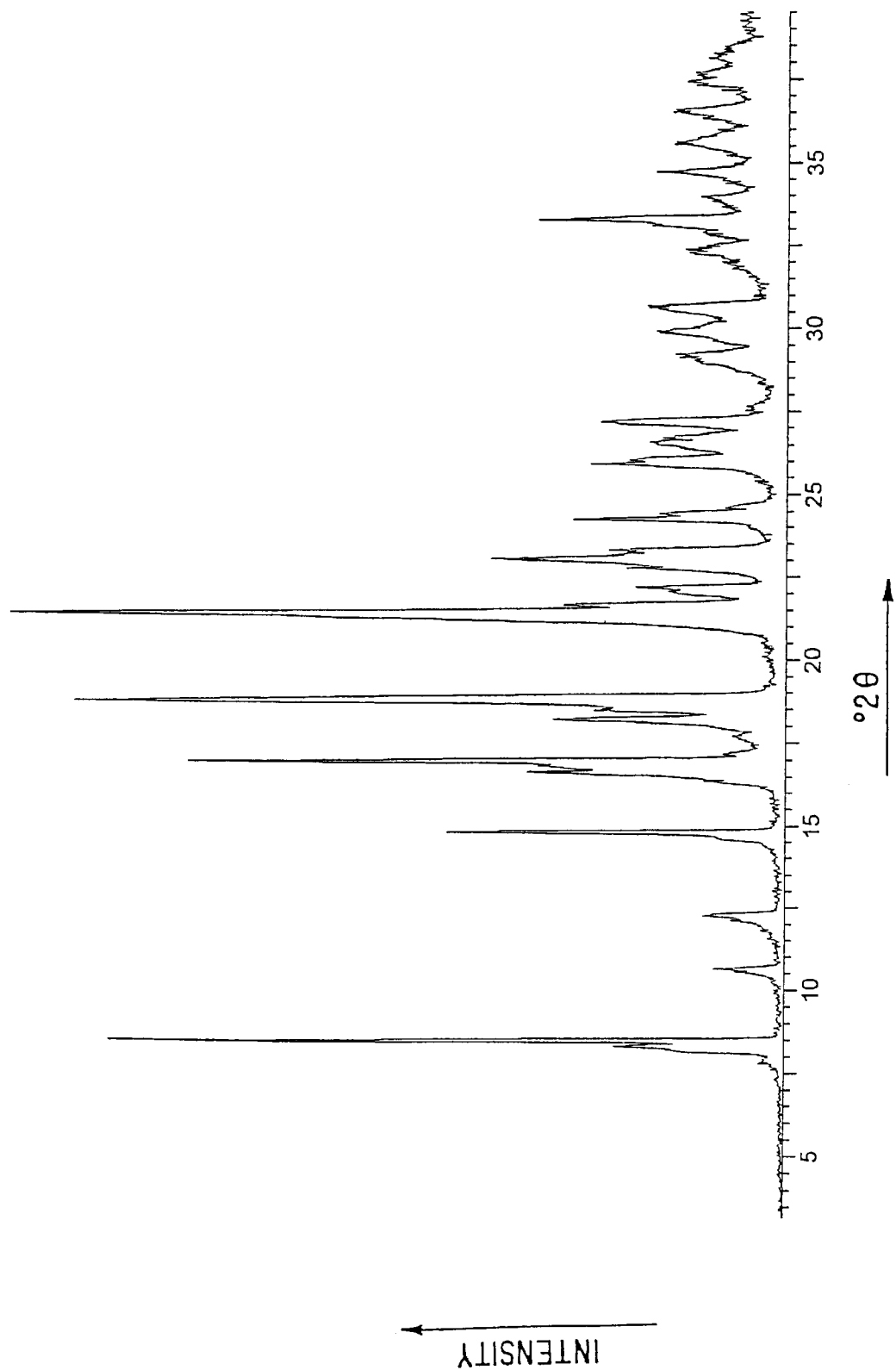
FIG. 1 is an X-ray powder diffraction pattern of Form A of 4-benzyl-2-hydroxy-1,4-oxazin-3-one.

The present invention is directed to 4-benzyl-2-hydroxy-1,4-oxazin-3-one of the formula:

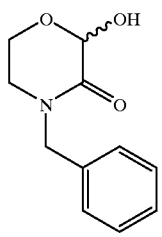

A general process for the preparation of 4-benzyl-2-hydroxy-1,4-oxazin-3-one is as follows:

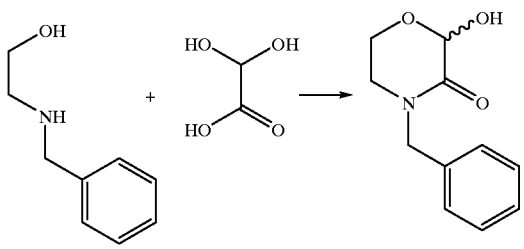

In accordance with this process, the treatment of N-benzylethanolamine with glyoxylic acid in a solvent provides 4-benzyl-2-hydroxy-1,4-oxazin-3-one in higher yields and in a more efficient route than the processes disclosed in the art.

The reaction between glyoxylic acid and N-benzylethanolamine occurs via the following intermediate:

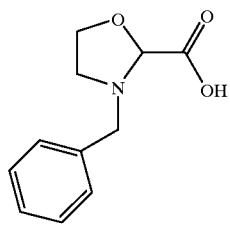

This intermediate can be isolated in high yield when the starting materials are mixed at ambient temperature. Heating of the isolated intermediate in various solvents yields 4-benzyl-2-hydroxy-1,4-oxazin-3-one. It is preferred that the processes to 4-benzyl-2-hydroxy-1,4-oxazin-3-one are conducted out in a single reaction vessel without isolation of this intermediate.

The present invention is further directed to a compound of the formula:

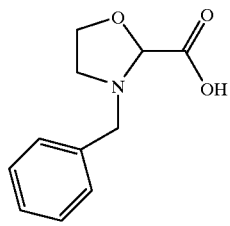

The compound 4-benzyl-2-hydroxy-1,4-oxazin-3-one of the formula:

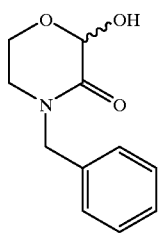

may be prepared by a process which comprises:
reacting N-benzylethanolamine of the formula:

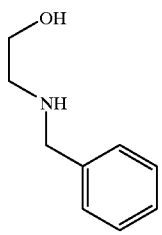

with glyoxylic acid of the formula:

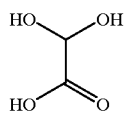

to give 4-benzyl-2-hydroxy-1,4-oxazin-3-one of the formula:

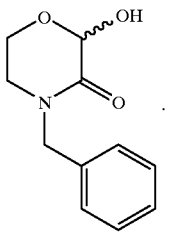

In this process it is preferred that the solvent is selected from a water miscible solvent such as acetone, 2-butanone, dimethylformamide, N,N-dimethyl-acetamide, dimethylsulfoxide, a $C_1$–$C_3$ alcohol (such as methanol, ethanol, 1-propanol and 2-propanol), N-methylpyrrolidinone, 1,4-dioxane, 1,3-dioxolane, tetrahydrofuran, acetonitrile, mixtures therof, and mixtures of these with water.

In the process it is more preferred that the solvent is selected from tetrahydrofuran, acetonitrile, mixtures thereof, and a mixtures of these with water.

An especially preferred solvent is a mixture of tetrahydrofuran and water. In the present invention it is more preferred that the solvent is a mixture of tetrahdrofuran and water wherein the ratio of tetrahdrofuran: water is greater than 10:90 (v:v).

In the process it is preferred that the temperature of the reaction mixture is between about ambient room temperature and about 100° C., more preferably in between about 60 to about 70° C. The most preferred temperature is that of refluxing THF/$H_2O$ mixtures (about 65–70° C.).

Glyoxylic acid can be used either as solid glyoxylic acid monohydrate or as a solution in water. A 50 wt % solution of glyoxylic acid in water is commercially available and is the most preferred.

The compound 4-benzyl-2-hydroxy-1,4-oxazin-3-one of the formula:

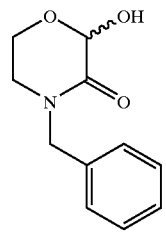

may also be prepared by a process which comprises:
reacting N-benzylethanolamine of the formula:

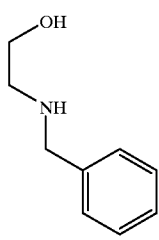

with a compound of the formula:

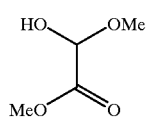

in a solvent which comprises an alcohol, such as methanol, to give 4-benzyl-2-hydroxy-1,4-oxazin-3-one of the formula:

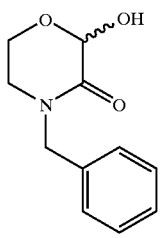

The compound 4-benzyl-2-hydroxy-1,4-oxazin-3-one of the formula:

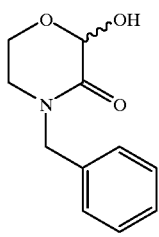

may also be prepared by a process which comprises:

reacting N-benzylethanolamine of the formula:

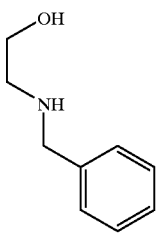

with a compound of the formula:

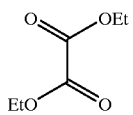

in a solvent which comprises an alcohol, such as ethanol, and an alkane, such as hexanes, to give a compound of the formula:

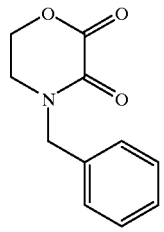

followed by reduction of the compound with a reducing agent such as lithium tri(sec-butyl)borohydride in a solvent such as tetrahydrofuran to give 4-benzyl-2-hydroxy-1,4-oxazin-3-one of the formula:

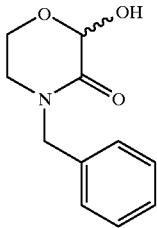

The compound 4-benzyl-2-hydroxy-1,4-oxazin-3-one of the formula:

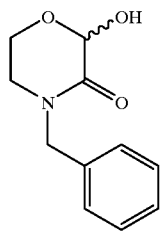

may be present in polymorphic forms. As used herein, a polymorphic form of a chemical compound is the same chemical entity, but in a different crystalline arrangement.

Preferred polymorphic forms of 4-benzyl-2-hydroxy-1,4-oxazin-3-one are described herein. These polymorphic forms have advantages in terms of thermodynamic stability and processability. For example, Form A of 4-benzyl-2-hydroxy-1,4-oxazin-3-one is more thermodynamically stable than Form B of 4-benzyl-2-hydroxy-1,4-oxazin-3-one.

The 4-benzyl-2-hydroxy-1,4-oxazin-3-one obtained in accordance with the present invention may be used as starting material in further reactions directly or following purification.

The starting materials and reagents for the subject processes are either commercially available or are known in the literature or may be prepared following literature methods described for analogous compounds. The skills required in carrying out the reaction and purification of the resulting reaction products are known to those in the art. Purification procedures include crystallization, distillation, normal phase or reverse phase chromatography.

The following examples are provided for the purpose of further illustration only and are not intended to be limitations on the disclosed invention.

EXAMPLE 1

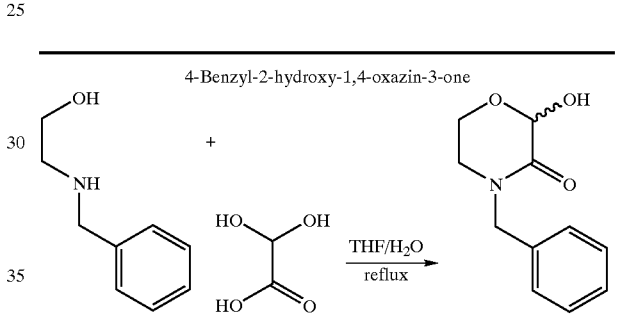

| Materials | MW | Density | Amount | mol | Equiv. |
|---|---|---|---|---|---|
| N-Benzylethanolamine (96%) | 151.21 | 1.065 | 7.80 kg | 49.5 (assay) | 1.0 |
| Glyoxylic acid (50% in water) | 74.04 | 1.342 | 12.60 L | 114.2 | 2.31 |
| Tetrahydrofuran | 72.11 | 0.889 | 27.0 L | — | — |
| 4-Benzyl-2-hydroxy-1,4-oxazin-3-one seed | 207.23 | — | 0.252 kg | 1.24 | 0.025 |
| Water | 18.0 | 1.00 | 63.0 L | — | — |

A solution of THF (27.0 L) and 50% aqueous glyoxylic acid (12.6 L; 16.9 kg) was heated to reflux and N-benzylethanolamine (7.8 kg) was added over 45 min. The resulting mixture was refluxed for 21 h. Then the THF was distilled under atmospheric pressure while maintaining a constant volume by simultaneous addition of water (27 L). Upon completion of the distillation (<8 vol % of THF in batch) the mixture was cooled from approximately 95–100 to 79–81° C. and was optionally seeded with 4-benzyl-2-hydroxy-1,4-oxazin-3-one (250 g). Upon further cooling to room temperature the product crystallized. Crystalline 4-benzyl-2-hydroxy-1,4-oxazin-3-one was filtered, washed with water and then dried in a vacuum oven at about 60° C. under a stream of $N_2$ (72–76% yield); m.p. 134° C.

$^1$H NMR (400 MHz, CDCl$_3$) δ 3.11 (ddd, J=12.5, 3.6 2.4 Hz, 1H), 3.45 (ddd, J=12.5, 10.8, 4.4 Hz, 1 H), 3.78 (ddd, J=12.1, 4.4, 2.4 Hz, 1H), 4.29 (ddd, J=12.1, 10.8, 3.6 Hz, 1H), 4.51 (d, J=14.5 Hz, 1H), 4.73 (d, J=14.5 Hz, 1H), 5.40 (s, 1H), 5.76 (br s, 1H), 7.26–7.37 (m, 5H); $^{13}$C NMR (100 MHz, CDCl$_3$) δ 45.6, 49.9, 57.6, 90.5, 127.9, 128.3 (2C), 128.9 (2C), 135.6, 167.3. $^1$H NMR [400 MHz, $(CD_3)_2SO$]δ 3.10 (ddd, J=12.4, 3.8 2.0 Hz, 1H), 3.34 (ddd, J=12.4, 11.2, 4.8 Hz, 1 H), 3.68 (ddd, J=12.0, 4.8, 2.0 Hz, 1H), 4.10 (ddd, J=12.0, 11.2, 3.8 Hz, 1H), 4.46 (d, J=14.8 Hz, 1H), 4.55 (d, J=14.8 Hz, 1H), 5.06 (d, J=6.2 Hz, 1H), 7.15 (d, J=6.2 Hz, 1-OH), 7.23–7.36 (m, 5H); $^{13}$C NMR [100 MHz, $(CD_3)_2SO$] δ 46.0, 49.1, 56.6, 90.6, 127.8, 128.1 (2C), 129.0 (2C), 137.2, 166.2.

Two polymorphic forms of 4-benzyl-2-hydroxy-1,4-oxazin-3-one (Form A and B) are characterized below by virtue of their X-Ray Powder Diffraction (XRPD) patterns. The XRPD patterns were collected on a Philips PW 3710 MPD control automated powder diffractometer. The x-ray generator employed a copper target, an accelerating potential of 45 kV and a filament emission of 40 mA. Diffraction patterns were collected from 2 to 40 degrees.

Form A of 4-benzyl-2-hydroxy-1,4-oxazin-3-one (m.p. 136° C.) was characterized by an X-ray powder diffraction pattern with key reflections at approximately: 8.45, 16.94, 18.16, and 21.41° (2 theta).

Additional XRPD data pertaining to this polymorphic form (Form A) is presented below in Table 1 (Generator settings: 45 kV, 40 mA; Cu alpha1, 2 wave lengths 1.54060, 1.54439 Ang) and in FIG. 1.

TABLE 1

| Peak No. | D Spacing (Ang) | I/Imax (%) |
|---|---|---|
| 1 | 10.45 | 89.8 |
| 2 | 5.99 | 45.0 |
| 3 | 5.34 | 33.5 |
| 4 | 5.23 | 77.9 |
| 5 | 4.88 | 29.7 |
| 6 | 4.81 | 25.2 |
| 7 | 4.74 | 91.5 |
| 8 | 4.70 | 51.6 |
| 9 | 4.15 | 100.0 |
| 10 | 4.10 | 28.8 |
| 11 | 3.87 | 36.8 |
| 12 | 3.67 | 28.1 |
| 13 | 3.44 | 25.6 |
| 14 | 2.69 | 32.3 |

Form B of 4-benzyl-2-hydroxy-1,4-oxazin-3-one (m.p. 134° C.) was characterized by an X-ray powder diffraction pattern with key reflections at approximately: 16.56, 18.88, 19.36 and 23.56° (2 theta).

Figure 2:
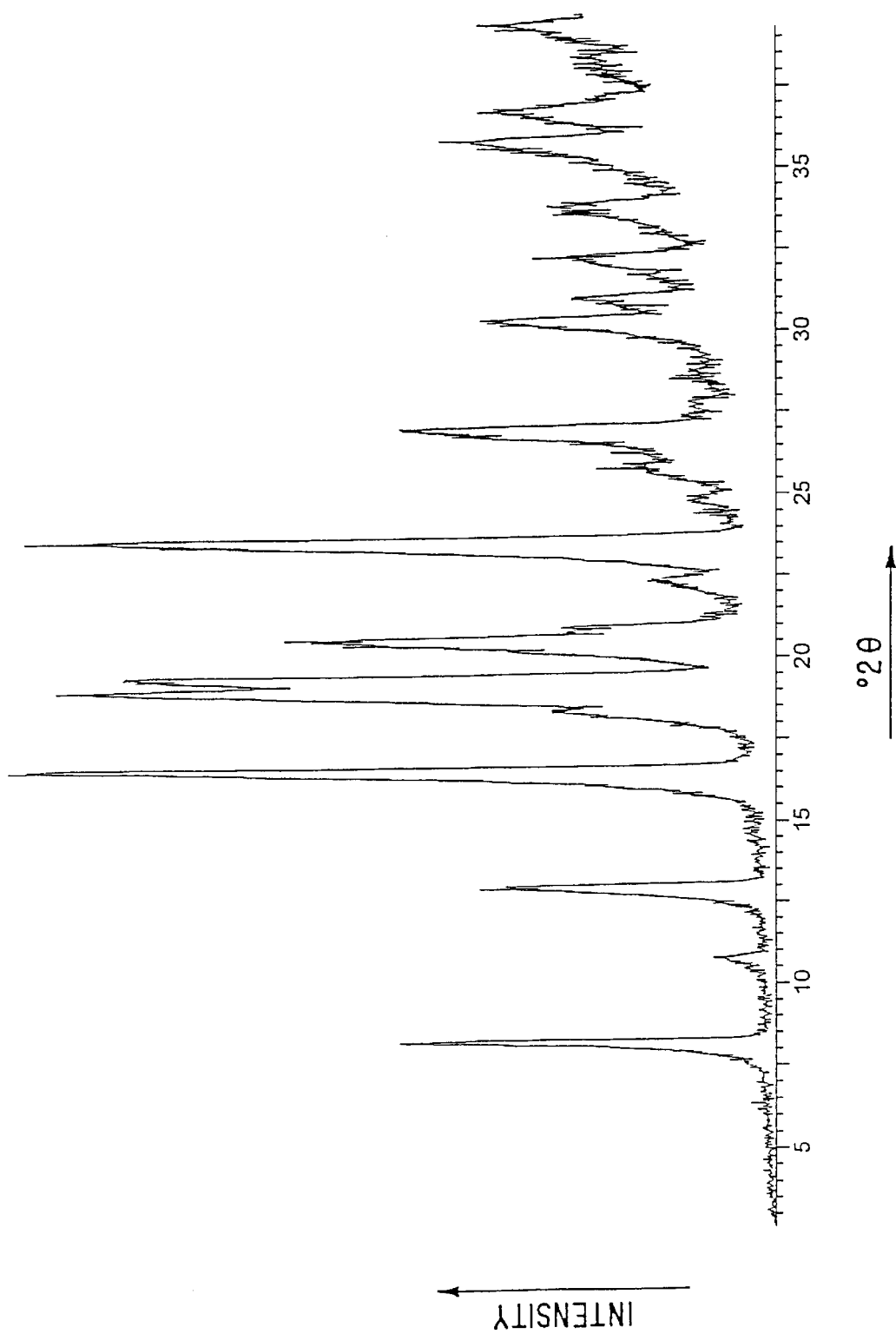
FIG. 2 is an X-ray powder diffraction pattern of Form B of 4-benzyl-2-hydroxy-1,4-oxazin-3-one.

Additional XRPD data pertaining to this polymorphic form (Form B) is presented below in Table 2 (Generator settings: 45 kV, 40 mA; Cu alpha1, 2 wave lengths 1.54060, 1.54439 Ang) and in FIG. 2.

TABLE 2

| Peak No. | D Spacing (Ang) | I/Imax (%) |
|---|---|---|
| 1 | 10.71 | 41.6 |
| 2 | 6.83 | 37.4 |
| 3 | 5.35 | 90.0 |
| 4 | 4.70 | 100.0 |
| 5 | 4.58 | 92.9 |
| 6 | 4.32 | 60.2 |
| 7 | 3.77 | 91.7 |
| 8 | 3.34 | 40.6 |
| 9 | 3.30 | 49.0 |
| 10 | 2.95 | 37.7 |
| 11 | 2.51 | 40.8 |
| 12 | 2.44 | 36.0 |

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, reaction conditions other than the particular conditions as set forth herein above may be applicable as a consequence of variations in the reagents or methodology to prepare the compounds from the processes of the invention indicated above. Likewise, the specific reactivity of starting materials may vary according to and depending upon the particular substituents present or the conditions of manufacture, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A compound of the formula:

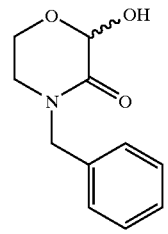

2. A polymorphic form of a compound of the formula:

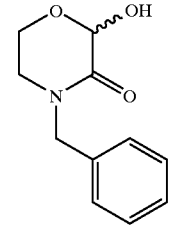

which is characterized by an X-ray powder diffraction pattern with key reflections at approximately: 8.45, 16.94, 18.16 and 21.41° (2 theta).

3. The polymorphic form of claim 2 which is further characterized by a melting point of 136° C.

4. A polymorphic form of a compound of the formula:

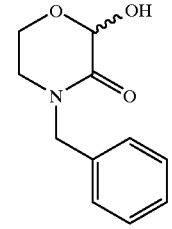

which is characterized by an X-ray powder diffraction pattern with key reflections at approximately: 16.56, 18.88, 19.36 and 23.56° (2 theta).

5. The polymorphic form of claim 3 which is further characterized by a melting point of 134° C.

6. A compound of the formula:

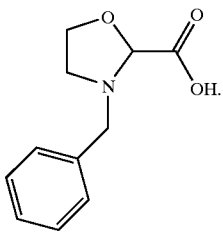

7. A process for the preparation of a compound of the formula:

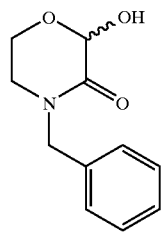

which comprises:

reacting N-benzylethanolamine of the formula:

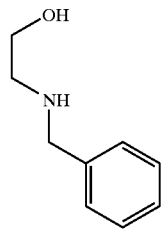

with glyoxylic acid of the formula:

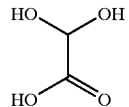

in a solvent to give the compound of the formula:

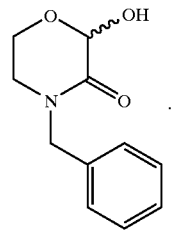

8. The process of claim 7 wherein the solvent comprises: acetone, 2-butanone, dimethylformamide, N,N-dimethylacetamide, dimethylsulfoxide, methanol, ethanol, 1-propanol, 2-propanol, N-methylpyrrolidinone, 1,4-dioxane, 1,3-dioxolane, tetrahydrofuran, acetonitrile, mixtures therof, and mixtures of these with water.

9. The process of claim 7 wherein the solvent comprises: tetrahydrofuran, acetonitrile, mixtures thereof, and a mixtures of these with water.

10. The process of claim 7 wherein the solvent comprises a mixture of tetrahydrofuran and water.

11. The process of claim 7 wherein the temperature of the reaction mixture is between about ambient room temperature and about 100° C.

12. The process of claim 7 wherein the glyoxylic acid employed is present as a solution in water.

13. The process of claim 7 which comprises the additional step of isolating the intermediate compound of the formula:

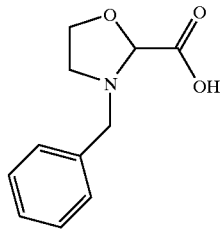

followed by heating such compound in a solvent to give the 4-benzyl-2-hydroxy-1,4-oxazin-3-one.

14. A process for the preparation of 4-benzyl-2-hydroxy-1,4-oxazin-3-one which comprises:
reacting N-benzylethanolamine with glyoxylic acid in a mixture of tetrahydrofuran and water at solvent reflux, to give 4-benzyl-2-hydroxy-1,4-oxazin-3-one.

* * * * *